(12) United States Patent
Gorham et al.

(10) Patent No.: US 7,226,436 B2
(45) Date of Patent: Jun. 5, 2007

(54) CARDBOARD TAMPON APPLICATOR WITH OPTICAL ENHANCING MATERIAL COATED ON INNER LAYERS

(75) Inventors: Patrick Gorham, Wyoming, DE (US); Keith Edgett, Middletown, DE (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 11/075,169

(22) Filed: Mar. 8, 2005

(65) Prior Publication Data

US 2005/0197617 A1 Sep. 8, 2005

Related U.S. Application Data

(60) Provisional application No. 60/551,109, filed on Mar. 8, 2004.

(51) Int. Cl.
*A61F 13/32* (2006.01)
*A61F 13/20* (2006.01)

(52) U.S. Cl. .................. 604/385.17; 604/904; 604/11; D24/141

(58) Field of Classification Search .......... 604/385.17, 604/904, 11–15; 600/29; D24/141; 206/529
See application file for complete search history.

(56) References Cited

U.S. PATENT DOCUMENTS

| | | | |
|---|---|---|---|
| 2,489,502 A | 11/1949 | Ruth | |
| 2,587,717 A | 3/1952 | Fourness | |
| 2,910,482 A | 10/1959 | Gottlieb | |
| 3,071,482 A | 1/1963 | Miller | |
| 3,390,671 A | 7/1968 | Hildebrand | |
| 3,433,225 A | 3/1969 | Voss et al. | |
| 3,464,648 A * | 9/1969 | Fuhriman | 242/139 |
| 3,628,533 A | 12/1971 | Loywer | |
| 3,674,025 A * | 7/1972 | Bleuer | 604/12 |
| 3,717,149 A | 2/1973 | Morane | |
| 3,753,437 A | 8/1973 | Hood et al. | |
| 3,760,808 A | 9/1973 | Bleuer | |
| 3,762,413 A | 10/1973 | Hanke | |
| 3,819,566 A | 6/1974 | Pinsky et al. | |
| 3,830,236 A | 8/1974 | Hanke | |
| 3,861,946 A | 1/1975 | Waitkins et al. | |
| 3,895,643 A | 7/1975 | Berger et al. | |
| 4,027,673 A | 6/1977 | Poncy et al. | |
| 4,038,099 A | 7/1977 | DeLuca, Jr. et al. | |
| 4,077,409 A | 3/1978 | Murray et al. | |
| 4,088,132 A | 5/1978 | Wood et al. | |
| 4,205,995 A | 6/1980 | Wheeler et al. | |
| 4,412,833 A | 11/1983 | Wiegner et al. | |
| 4,453,925 A | 6/1984 | Decker | |
| 4,508,531 A | 4/1985 | Whitehead | |
| 4,543,086 A | 9/1985 | Johnson | |
| 4,650,459 A | 3/1987 | Sheldon | |
| 4,676,773 A | 6/1987 | Sheldon | |
| 4,699,610 A | 10/1987 | Hanano et al. | |
| 4,787,895 A | 11/1988 | Stokes et al. | |
| 4,792,326 A | 12/1988 | Tews | |

(Continued)

*Primary Examiner*—Tatyana Zalukaeva
*Assistant Examiner*—Laura C. Hill
(74) *Attorney, Agent, or Firm*—Ohlandt, Greeley, Ruggiero & Perle, L.L.P.

(57) ABSTRACT

A multiple-layered tampon applicator that has at least one modification to one or more inner layers that form the applicator. As a result, enhanced aesthetics, enhanced functionality, or both are achieved in the applicator.

30 Claims, 2 Drawing Sheets

U.S. PATENT DOCUMENTS

| | | | |
|---|---|---|---|
| 4,857,044 A | 8/1989 | Lennon | |
| 4,872,933 A | 10/1989 | Tews | |
| 4,900,299 A | 2/1990 | Webb | |
| 4,973,302 A | 11/1990 | Armour et al. | |
| 5,002,526 A | 3/1991 | Herring | |
| 5,087,239 A | 2/1992 | Beastall et al. | |
| 5,153,971 A | 10/1992 | Van Iten | |
| 5,158,535 A | 10/1992 | Paul et al. | |
| 5,267,953 A | 12/1993 | Paul et al. | |
| 5,279,541 A | 1/1994 | Frayman et al. | |
| 5,290,501 A | 3/1994 | Klesius | |
| 5,330,421 A | 7/1994 | Tarr et al. | |
| 5,346,468 A * | 9/1994 | Campion et al. | 604/13 |
| 5,348,534 A | 9/1994 | Tomaszewski et al. | |
| 5,350,354 A | 9/1994 | Billmers | |
| 5,376,698 A | 12/1994 | Sipsas et al. | |
| 5,389,067 A * | 2/1995 | Rejai | 604/14 |
| 5,389,068 A | 2/1995 | Keck | |
| 5,393,339 A | 2/1995 | Gerson et al. | |
| 5,395,308 A * | 3/1995 | Fox et al. | 604/15 |
| 5,437,628 A | 8/1995 | Fox et al. | |
| 5,456,749 A | 10/1995 | Iwasa et al. | |
| 5,501,063 A | 3/1996 | Tews et al. | |
| 5,532,350 A | 7/1996 | Cottrell et al. | |
| 5,533,990 A | 7/1996 | Yeo | |
| 5,554,108 A | 9/1996 | Browning et al. | |
| 5,558,631 A | 9/1996 | Campion et al. | |
| 5,569,177 A | 10/1996 | Fox et al. | |
| 5,571,567 A | 11/1996 | Shah | |
| 5,599,293 A | 2/1997 | Orenga et al. | |
| 5,601,530 A * | 2/1997 | Nielsen et al. | 604/11 |
| 5,643,196 A | 7/1997 | Child et al. | |
| 5,683,358 A | 11/1997 | Nielson et al. | |
| 5,693,009 A | 12/1997 | Fox et al. | |
| 5,702,553 A | 12/1997 | Iskra et al. | |
| 5,709,652 A | 1/1998 | Hagerty | |
| 5,738,646 A | 4/1998 | Fox et al. | |
| 5,746,710 A | 5/1998 | Nielson et al. | |
| 5,766,145 A | 6/1998 | Fox et al. | |
| 5,782,793 A | 7/1998 | Nielson et al. | |
| 5,782,794 A * | 7/1998 | Assenheimer Downs | 604/15 |
| 5,788,663 A | 8/1998 | Igaue et al. | |
| 5,792,096 A | 8/1998 | Rentmeester et al. | |
| 5,795,320 A | 8/1998 | Nielson et al. | |
| 5,800,377 A | 9/1998 | Campion et al. | |
| 5,804,616 A | 9/1998 | Mowrer et al. | |
| 5,817,047 A | 10/1998 | Osborn, III et al. | |
| 5,827,214 A | 10/1998 | Fox et al. | |
| 5,827,251 A | 10/1998 | Moder et al. | |
| 5,873,971 A | 2/1999 | Balzar | |
| 5,891,081 A | 4/1999 | McNelis et al. | |
| 5,891,127 A | 4/1999 | Moder et al. | |
| 5,928,183 A | 7/1999 | Fox et al. | |
| 5,931,803 A | 8/1999 | Jackson | |
| 5,954,683 A | 9/1999 | Downs et al. | |
| 5,964,741 A | 10/1999 | Moder et al. | |
| 5,984,888 A | 11/1999 | Nielsen et al. | |
| 6,019,743 A | 2/2000 | Cole et al. | |
| 6,024,716 A | 2/2000 | Rejai | |
| 6,045,526 A * | 4/2000 | Jackson | 604/15 |
| 6,056,714 A | 5/2000 | McNelis et al. | |
| 6,068,899 A | 5/2000 | Osborn, III et al. | |
| 6,095,998 A | 8/2000 | Osborn, III et al. | |
| 6,095,999 A | 8/2000 | Jackson et al. | |
| 6,171,426 B1 | 1/2001 | Blanchard | |
| 6,179,802 B1 | 1/2001 | Jackson | |
| 6,196,988 B1 | 3/2001 | Cole et al. | |
| 6,217,542 B1 | 4/2001 | Stevens et al. | |
| 6,221,497 B1 | 4/2001 | Roman et al. | |
| 6,248,089 B1 | 6/2001 | Porat | |
| 6,264,626 B1 * | 7/2001 | Linares et al. | 604/15 |
| 6,302,861 B2 | 10/2001 | Tweddell, III et al. | |
| 6,322,531 B1 | 11/2001 | Cortese | |
| 6,355,011 B2 | 3/2002 | Suga | |
| 6,358,223 B1 | 3/2002 | Mackay et al. | |
| 6,368,399 B1 | 4/2002 | Aoba et al. | |
| 6,368,442 B1 * | 4/2002 | Linares et al. | 156/198 |
| 6,383,161 B1 | 5/2002 | Balzar et al. | |
| 6,432,075 B1 | 8/2002 | Wada et al. | |
| 6,432,076 B1 | 8/2002 | Wada et al. | |
| 6,450,985 B1 | 9/2002 | Schoelling et al. | |
| 6,450,986 B1 | 9/2002 | Binner et al. | |
| 6,458,064 B1 | 10/2002 | Balzar et al. | |
| 6,478,764 B1 | 11/2002 | Suga | |
| 6,508,966 B1 | 1/2003 | Castro et al. | |
| 6,511,451 B1 | 1/2003 | Schoelling et al. | |
| 6,511,452 B1 * | 1/2003 | Rejai et al. | 604/15 |
| 6,524,269 B2 | 2/2003 | McNamara | |
| 6,533,748 B2 | 3/2003 | Buzot | |
| 6,545,065 B2 | 4/2003 | Solms et al. | |
| 6,545,283 B2 | 4/2003 | Williams et al. | |
| 6,572,577 B1 | 6/2003 | Binner et al. | |
| 6,610,025 B2 | 8/2003 | Berg et al. | |
| 6,648,846 B2 | 11/2003 | Binner et al. | |
| 6,730,057 B2 * | 5/2004 | Zhao et al. | 604/11 |
| 2002/0042599 A1 | 4/2002 | Zhao et al. | |
| 2002/0107305 A1 | 8/2002 | Edler | |
| 2002/0107494 A1 | 8/2002 | Williams | |
| 2002/0117080 A1 | 8/2002 | Okutsu et al. | |
| 2002/0138035 A1 | 9/2002 | Hull, Jr. | |
| 2002/0143287 A1 | 10/2002 | Buzot | |
| 2002/0183681 A1 * | 12/2002 | Bernard | 604/15 |
| 2003/0028177 A1 | 2/2003 | Berg et al. | |
| 2003/0036721 A1 | 2/2003 | Zhao et al. | |
| 2003/0047118 A1 | 3/2003 | Perry et al. | |
| 2003/0073948 A1 | 4/2003 | Binner et al. | |
| 2003/0125416 A1 | 7/2003 | Munro et al. | |
| 2003/0181844 A1 | 9/2003 | Bernard | |

* cited by examiner

CARDBOARD TAMPON APPLICATOR WITH OPTICAL ENHANCING MATERIAL COATED ON INNER LAYERS

RELATED APPLICATION

The present application claims priority to pending U.S. Provisional Patent Application bearing Ser. No. 60/551,109, filed on Mar. 8, 2004.

BACKGROUND OF INVENTION

1. Field of the Invention

The present invention relates generally to a multiple-layered tampon applicator. More particularly, the present invention relates to a multiple-layered tampon applicator with a modified inner layer(s), which results in improved functionality and aesthetics.

2. Description of Related Art

There exist numerous applications that require a product to possess both highly functional properties in conjunction with highly aesthetic properties. This is especially true with consumer products, where the consumer is not only concerned with how well the particular product functions, but also how the product looks and feels.

In particular, feminine hygiene products, such as tampons, are subject to above-identified constraints, making it extremely difficult to make a product that is highly functional, yet meets the aesthetic demands of the consumer.

Through consumer studies, it has been determined that tampon applicator color, texture and finish can alter a user's perception of insertion ease and comfort of said applicator. This includes, but is not limited to, impartation of pigment, modification of surface texture, coefficient of friction, surface contact points, and visual effects due to reflection of light.

With regard to tampon applicators, it is widely known that they are generally formed from either a molded thermoplastic material, such as plastic, or a paper laminate, such as cardboard or paperboard.

Liquid coated paper laminate applicators are known in the art. For example, U.S. Pat. No. 4,412,833 to Weigner et al. is directed to an applicator formed of a high-gloss paper that can be coated with a degradable, dispersible or water soluble polymer, such as a modified polyethylene, polypropylene, polyvinylidene chloride or polyvinyl alcohol. U.S. Pat. No. 4,508,531 to Whitehead provides an applicator with a heat-sensitive coating, such as polyolefin (e.g., polyethylene or polypropylene) or a heat sensitive adhesive. U.S. Pat. No. 5,984,888 to Nielson et al. is directed to a paper applicator article having multiple paper layers and a compostable coating on the exterior surface.

However, neither the liquid nor film coatings applied to the prior art cardboard tampon applicators described above have permitted the combination of the formation of the desired glossy finish, retention of applicator circularity, reduction in friction, and sufficient biodegradability, let alone while further providing enhanced aesthetics to the applicator. Further, some prior art liquid coatings are more expensive, and require the use of organic solvents, leading to higher manufacturing cost and consumer cost.

The present invention overcomes the difficulties in providing additional aesthetic properties and/or additional functional properties to a tampon applicator without compromising the desired functional properties associated with the outer or exterior surface of the tampon applicator. This is accomplished by modifying at least one inner layer of material that forms the multiple-layer applicator. As a result, a highly functional product having enhanced aesthetics and or functionality is efficiently produced without compromising any of the desired functional properties associated with the exterior surface.

SUMMARY OF THE INVENTION

It is an object of the present invention to provide a multi-layered tampon applicator with one or more inner layers having one or more modifications.

It is another object of the present invention to provide such a tampon applicator where the one or more modifications provide enhanced aesthetics to the applicator.

It is still another object of the present invention to provide such a tampon applicator where the one or more modifications provide enhanced functional properties to the tampon applicator.

It is yet another object of the present invention to provide such a tampon applicator where the one or more modifications provide a combination of enhanced aesthetics and enhanced functionality to the tampon applicator.

These and other objects and advantages of the present invention will be appreciated from a tampon applicator according to the present invention. The multiple-layered tampon applicator has at least one modification to one or more inner layers that form the applicator. As a result, enhanced aesthetics, enhanced functionality, or both are achieved.

DETAILED DESCRIPTION OF THE INVENTION

Figure 1:
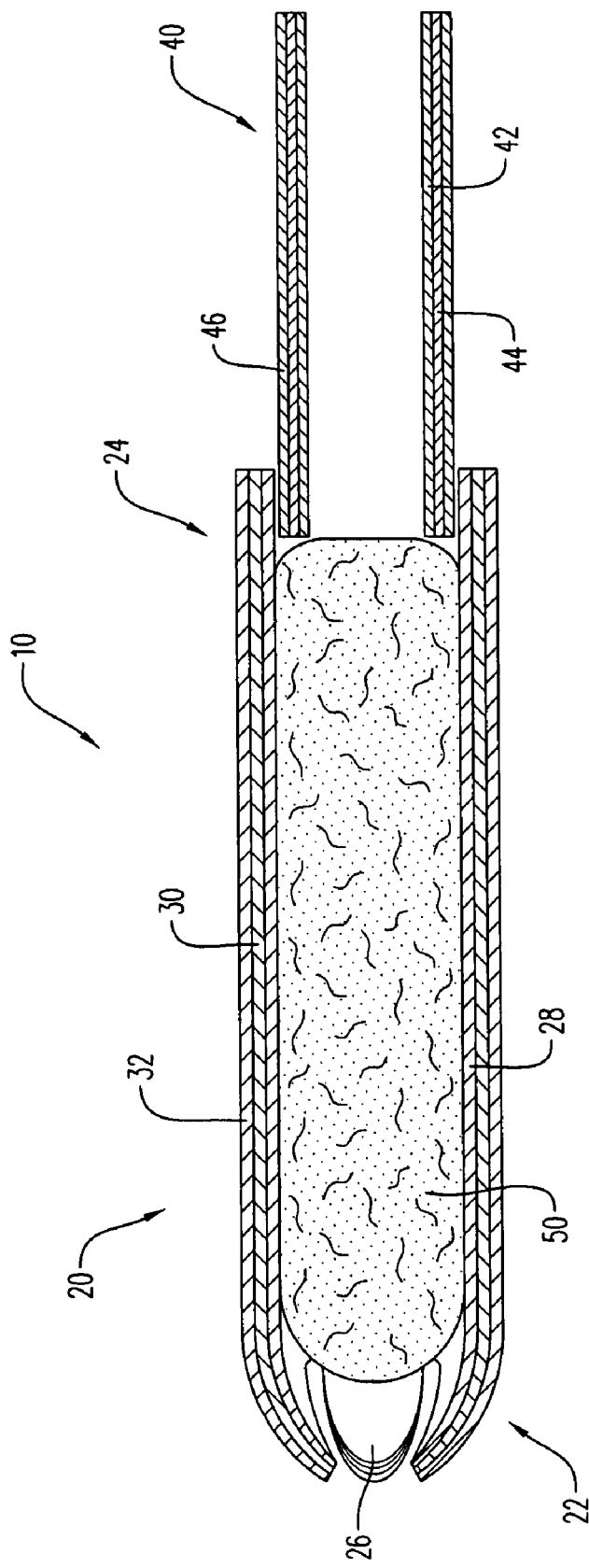
FIG. 1 is a cross-sectional view of a multiple-layer tampon applicator according to the present invention.

The multiple-layered tampon applicator of the present invention, as a result of one or more inner layer modifications, possess, for example, improved visual/aesthetic properties, improved surface characteristics and/or improved perception of insertion comfort.

The term "applicator" is meant to include a barrel and/or a plunger. The barrel includes a withdrawal end and an insertion end opposite the withdrawal end and is capable of housing a pledget. The withdrawal end may include a fingergrip portion or feature(s), while the insertion end may include a plurality of petals. The fingergrip portion and or the petals may be either integrally formed with the barrel or separately formed and secured to the barrel. By way of example, referring to FIG. 1, tampon applicator 10 is depicted with barrel 20 and plunger 40. Barrel 20 has insertion end 22 and withdrawal end 24. Insertion end 22 includes petals 26. Barrel 20 is shown housing a pledget 50.

The term "inner layer" is meant to refer to any layer except for the outermost or exterior layer of the applicator. A "layer" may include, but is not limited to, a coating, laminate, film, sheet, lacquer, non-woven fabric, mesh, paper, plastic, adhesive, or any other structure that forms any portion of the multiple-layered structure of the tampon applicator barrel or plunger. By way of example, again referring to FIG. 1, tampon applicator 10 has barrel 20 and plunger 40. Barrel 20 is formed from multiple-layers, including inner layers 28, 30. Plunger 40 is also formed from multiple layers, including inner layers 42, 44.

The terms "outer layer" or "outermost layer" are interchangeable and in the context of this application define the final layer of material that forms the outermost or exterior surface of the applicator barrel and/or applicator plunger. This is not to say, however, that any portion of the one or more inner layer modifications may protrude through the outer layer. By way of example, tampon applicator 10 depicted in FIG. 1 has barrel 20 and plunger 40. Barrel 20 includes outer layer 32 and plunger 40 includes outer layer 46.

It should be understood that while the multiple-layer tampon applicator 10 depicted in FIG. 1 is depicted with two inner layers, any number of inner layers may be used to form a multiple-layered tampon applicator that achieves the desired aesthetic and/or functional properties, according to the present invention.

Inner Layer(s) and Modification(s)

According to the present invention there are numerous, novel modifications that can be made to one or more inner layers of a tampon applicator to achieve the desired effect(s).

In one embodiment of the present invention, one or more inner layers are modified to optically enhance the applicator. Suitable material for optically enhancing the applicator includes, but is not limited to, coatings, cast-coated paper, colored (dyed or pigmented) paper, embossed paper, paper impregnated with optical enhancing material, gate rolled paper, release paper, tissue paper, pigmented wax, wax with lip gloss colorants, lacquer, mica, $TiO_2$-coated mica, metal oxide, bismuth oxychloride, polymers, polymer blends, copolymers, polymer coatings, pigments, dyes, colorants, holographic, pearlescent, reflective, glitter, plasticizer, softener, elasticizer, or any combinations of the above.

In an embodiment of the present invention, the one or more inner layers may include a coating composition such as, but not limited to, resin, wax or any combinations thereof. Suitable resin for use in the present invention includes, but is not limited to, epoxy, acrylic, urethane, polyester, silicone, UV curable epoxy, UV curable acrylic, electron beam curable epoxy, electron beam curable acrylic, UV curable silicone, electron beam curable silicone, thermally curable silicone, modified resins such as styrenated acrylic, epoxy acrylate, polyester acrylate, polyester, vinyl ester, vinyl ether, vinyl chloride, polyvinyl alcohol, polyvinyl acetate, and any modifications or combinations thereof.

By way of example, U.S. Pat. No. 5,931,803, incorporated by reference herein in its entirety, discloses UV curable epoxy blends suitable for use in the present invention. Also, by way of example, U.S. Pat. No. 6,221,497, incorporated by reference herein in its entirety, discloses UV curable epoxy blends suitable for use in the coating composition of the present invention.

To effectuate one or more optical enhancements, the coating composition may include one or more optical components added to the resin and/or wax, which impart aesthetic properties to the coating composition. Such components may include, but are not limited to, mica, $TiO_2$-coated mica, iron oxide coated mica, bismuth oxychloride, holographic material, pearlescence material, reflective material, glitter, metallic effect pigment, interference pigment, liquid crystal effect material, or any combinations thereof. The above optical components may be natural or synthetic in origin. Preferably, the optical component used in the coating composition of the present invention is mica, $TiO_2$-coated mica, iron oxide coated mica, bismuth oxychloride, or any combination thereof.

When present, the one or more optical components are included in the coating composition in an amount about 1 weight percent (wt. %) to about 70 wt. %, based on the total weight of the coating composition. More preferably, the one or more optical components are present in an amount about 2 wt. % to about 25 wt. %, and most preferably about 5 wt. % to about 15 wt. %.

When bismuth oxychloride is used, it preferably has a particle size of about 8 to about 11 microns and is present in the coating composition in an amount about 5 wt. % to about 50 wt. %. More preferably, the bismuth oxychloride has a particle size of about 9 microns to about 10 microns and is present in an amount about 25 wt. % to about 35 wt. %.

For example, it has been found that the use of bismuth oxychloride, when carefully homogenized in the composition results in an improved dispersion. This improved dispersion imparts improved rub-resistance characteristics to the coating. In addition, the homogenized bismuth oxychloride particles also result in improved luster or brilliance characteristics in the coating composition, which results in improved appearance properties.

In another embodiment of the present invention the optical component used in the coating composition of the present invention is mica, $TiO_2$-coated mica, iron-oxide coated mica, or any combinations thereof. Preferably, the optical component is $TiO_2$-coated mica. Examples of suitable mica components include, but are not limited to, components sold by Engelhard under various tradenames including MAGNAPEARL, MEARLIN, MEARLITE, and LUMINA, and Merck's EM Chemicals division, which sells AFFLAIR.

Mica based pigments are irregularly shaped mica platelets that may be coated with titanium dioxide or iron oxide. When added to a coating composition according to the present invention, they produce a variety of pearlescent effects including a white lustrous to sparkly appearance, an interference or flop color that changes appearance with the viewing angle, or metallic silver and gold effects. $TiO_2$-coated mica may be made using both anatase and rutile grades of titanium dioxide. The rutile grade is preferred, as it produces a higher luster and better whiteness.

When mica, and particularly $TiO_2$-coated mica is used, it preferably has a particle size of about 2 microns to about 150 microns and is present in the coating composition in an amount about 1 wt. % to about 60 wt. %. More preferably, the mica has a particle size of about 2 microns to about 10 microns and is present in an amount about 2 wt. % to about 20 wt. %, and more preferably about 5 wt. % to about 15 wt. %.

The coating composition may include one or more color components either alone or in combination with one or more optical components to selectively impart a color to the coating composition. Suitable color components may include, but are not limited to, colorants, dyes, inorganic pigments, organic pigments, or any combinations thereof. Preferably, one or more pigments are included in the resin and/or wax to impart color. Suitable pigment may include, but is not limited to, titanium dioxide, white titanium dioxide, iron oxide, red iron oxide, orange iron oxide, white zinc sulfide, aluminum powder, bronze powder, Red Lake C, phthalocyanine green, phthalocyanine blue, phthalocyanine red, diarylide yellow, quinacridone red, rhodamine red, lithol rubine red, napthol red, neozapon red, carbizole violet, carbon black, or any combinations thereof.

When present, the one or more color components are included in the resin and/or wax in an amount about 0.001 wt. % to about 5 wt. %. Preferably, the one or more color components are present in an amount about 0.01 wt. % to about 3 wt. %, and more preferably about 0.5 wt. % to about 1 wt. %.

To form the coating composition, the one or more color components are blended into the coating composition. Special care must be taken when formulating the coating composition of the present invention to avoid adding the one or more color components in such an amount or manner that ultimately compromises the desired and/or required physical properties of the final coating composition.

By way of example, suitable material that may be used to optically enhance one or more inner layers include, but are not limited to, RAD-KOTE K261-Purple-Purple Tinted Varnish, RAD-KOTE K261-R1-Red Tinted Varnish, RAD-KOTE K261-Blue1-Blue Tinted Varnish, and pearlescent products 23KRCCV1-HLP30 (Purple, Pink & Blue) and K261P 1531 (Clear, Purple, Pink, & Blue). All of the above materials are commercially available from RadCure.

Further examples and descriptions of suitable coating material that would be useful in modifying one or more inner layers according to the present invention are described in co-pending utility patent application bearing Ser. No. 10/877,440, which claims the benefit of earlier filed provisional patent applications bearing Ser. Nos. 60/482,649; 60/502,432; and 60/536,100, all of which are incorporated by reference herein in their entirety.

In addition to or in place of the above, one or more surface modification materials may be included in/on one or more inner layers to improve vaginal insertion characteristics and/or grippability. Suitable surface modification materials include, but are not limited to, one or more lubricants, surface hardness/softness modifiers, abrasive materials, hydrophilic material, hydrophobic material, polyurethane, acrylic, PVC, silicone, PTFE, paraffin, phenol, fluoropolymer, polyester, epoxy, vinyl, polyamideimide, PPS, nylon, parylene, urethane, polyamide, polysulfide, Penford Gum 280 Starch, cast-coated paper, lubricious paper, sprayed paper, or any combinations of the above.

In a preferred embodiment, the one or more surface modification materials are one or more lubricants. Suitable lubricants that may be used in the present invention include, but are not limited to, glycerin, glycerides, triglycerides, mineral oils, vegetable oils, plant extracts, aloe, kiwi extract, silicones and any combinations thereof. By way of example, the following lubricants are suitable for use in the present invention: REPLENS sold by Columbia Labs; BIO-ACTIVE MULTI-GYN LUBRICARE sold by Multi-Gyn USA; K-Y Jelly, sold by Johnson and Johnson; ASTROGLIDE sold by Astro-Lube Inc.; SYLK; WET PLATINUM ORIGINAL; JUICY LUBE; AQUA LUBE sold by Mayer Labs; LIFESTYLES Liquid Personal Lubricant; LUBRIN sold by Upsher-Smith Laboratories, Inc.; TODAY PERSONAL LUBRICANT; and GYNE-MOISTRIN sold by Schering-Plough.

In addition to or in place of the above, one or more surface modifications may be included in/on one or more inner layers to improve vaginal insertion characteristics and/or grippability. Suitable surface modifications include, but are not limited to, physical/mechanical surface designs, etching, scratching, texture, embossments, depressions, protrusions, designs, branding, ornamental, gate-rolled material on paper, water mark, printed paper, or any combinations of the above.

It is also considered that any generally known mixing techniques of coatings, dyes, colorants, modifiers and additives, including dispersions, suspensions and homogeneous mixtures; printing patterns or embossments; coating techniques of outer surface materials such as lamination, topcoating, dipping, vacuum deposition, spraying, electrostatic spraying, powder coating, liquid coating, parylene coating; color-impartation techniques such as spraying color onto the surface; and/or surface finishes are possible methods of modifying the surface to achieve the effects listed above. It is considered that any materials used to achieve the effects described previously either form one or more inner layers and/or are integral with one or more inner layers of the tampon applicator of the present invention.

Outermost Layer

The outermost or exterior layer of the tampon applicator may be any suitable material and/or coating known to those skilled in the art. Suitable material and/or coating for use in the present invention include, but are not limited to, resin, wax, paper, plastic, or any combinations thereof. Suitable resin for use in the present invention includes, but is not limited to, epoxy, acrylic, urethane, polyester, silicone, UV curable epoxy, UV curable acrylic, electron beam curable epoxy, electron beam curable acrylic, UV curable silicone, electron beam curable silicone, thermally curable silicone, modified resins such as styrenated acrylic, epoxy acrylate, polyester acrylate, polyester, vinyl ester, vinyl ether, vinyl chloride, polyvinyl alcohol, polyvinyl acetate, and any modifications or combinations thereof.

By way of example, U.S. Pat. No. 5,931,803, incorporated by reference herein in its entirety, discloses UV curable epoxy blends suitable for use in the present invention. Also, by way of example, U.S. Pat. No. 6,221,497, incorporated by reference herein in its entirety, discloses UV curable epoxy blends suitable for use in the coating composition of the present invention.

The coating composition may also include one or more optical components added to the resin and/or wax, which impart aesthetic properties to the coating composition without compromising the ultimate functionality of the coating composition and subsequent coated tampon applicator. Such components may include, but are not limited to, mica, $TiO_2$-coated mica, iron oxide coated mica, bismuth oxychloride, holographic material, pearlescence material, reflective material, glitter, metallic effect pigment, interference pigment, liquid crystal effect material, or any combinations thereof. The above optical components may be natural or synthetic in origin. Preferably, the optical component used in the coating composition of the present invention is mica, $TiO_2$-coated mica, iron oxide coated mica, bismuth oxychloride, or any combination thereof.

When present, the one or more optical components are included in the coating composition in an amount about 1 weight percent (wt. %) to about 70 wt. %, based on the total weight of the coating composition. More preferably, the one or more optical components are present in an amount about 2 wt. % to about 25 wt. %, and most preferably about 5 wt. % to about 15 wt. %.

The coating composition may include one or more color components either alone or in combination with one or more optical components to selectively impart a color to the coating composition. Suitable color components may include, but are not limited to, colorants, dyes, inorganic pigments, organic pigments, or any combinations thereof. Preferably, one or more pigments are included in the coating composition to impart color. Suitable pigment may include, but is not limited to, titanium dioxide, white titanium dioxide, iron oxide, red iron oxide, orange iron oxide, white zinc sulfide, aluminum powder, bronze powder, Red Lake C, phthalocyanine green, phthalocyanine blue, phthalocyanine red, diarylide yellow, quinacridone red, rhodamine red, lithol rubine red, napthol red, neozapon red, carbizole violet, carbon black, or any combinations thereof.

When present, the one or more color components are included in the resin and/or wax in an amount about 0.001 wt. % to about 5 wt. %. Preferably, the one or more color components are present in an amount about 0.01 wt. % to about 3 wt. %, and more preferably about 0.5 wt. % to about 1 wt. %.

By way of example, suitable material that may be used to optically enhance one or more inner layers include, but are not limited to, RAD-KOTE K261-Purple-Purple Tinted Varnish, RAD-KOTE K261-R1-Red Tinted Varnish, RAD-KOTE K261-Blue1-Blue Tinted Varnish, and pearlescent products 23KRCCV1-HLP30 (Purple, Pink & Blue) and K261P 1531 (Clear, Purple, Pink, & Blue). All of the above materials are commercially available from RadCure. Examples of suitable mica components include, but are not limited to, components sold by Engelhard under various tradenames including MAGNAPEARL, MEARLIN, MEARLITE, and LUMINA, and Merck's EM Chemicals division, which sells AFFLAIR.

It has been unexpectedly found that the unique blend of resin and/or wax material with the one or more select color components results in a coating, that when applied to a substrate, demonstrates comparable and/or superior properties to a similar coating without the select color components. Moreover, the coating composition also exhibits similar properties, both functional and aesthetic, to those of plastic. This is especially important on cardboard tampon applicators coated with the coating composition.

It has also been surprisingly found that the coating composition exhibits an enhanced gloss. As a result, the coating composition has an enhanced visual appearance. Moreover, by way of example, when the coating composition is applied to a cardboard tampon applicator, the enhanced gloss gives the cardboard applicator a plastic-like appearance. The gloss, as measured at a 60° angle pursuant to ASTM D523, attributed to the coating composition of the present invention is in the range between about 30 to about 95, and preferably about 30 to about 60.

Another important attribute of the coating composition is that it possesses excellent colorfastness. The term colorfastness, as used herein, is the resistance of a material to change in any of its color characteristics, to transfer any of its colorant(s). to adjacent materials, or both, as a result of the exposure of the material to any environment that might be encountered during the processing, testing, storage, or use of the material. It is believed that the coating composition of the present invention would experience little to no color transfer, when tested pursuant to a test such as, for example, AATCC Test Method 8-1981.

Moreover, other key attributes of a coating composition, such as tensile strength, tensile modulus, and elongation, are not compromised by the coating composition according to the present invention, contrary to conventional wisdom.

Particularly, kinetic coefficient of friction measurements between about 0.1 to about 0.2 are achieved by coating compositions according to the present invention.

The coating composition provides the tampon applicator with not only a low coefficient of friction and high gloss, but also a colored, plastic-like appearance. Moreover, the coating has low extractables, which does not exceed 0.5 mg/in$^2$.

Once formulated, the coating composition can be applied to any one or more of the inner layers by any process known in the art of coating substrates. Suitable processes include, but are not limited to, spraying, topcoating, roll coating, dipping, printing, melting, extrusion, hot melt extrusion, slot die, knife, gravure, offset gravure, flexo, letterpress, offset and litho, screening, or any combinations thereof.

In the case of a cardboard tampon applicator according to the present invention, the coating composition that forms the outer layer is preferably applied to an outer surface of the one or more inner layers to form a base tampon applicator structure. The base tampon applicator structure, which includes the one or more modified inner layers and, preferably an outer layer, is formed into a tampon applicator product. The tampon applicator is preferably spiral wound; however, it could be formed as a convolute tube.

The coating composition that forms the outer layer can be applied to the entire applicator, or to any portion of the applicator desired. This may include any portion of the applicator, including any portion of the barrel and/or plunger. As a result, any desired property or properties may be selectively applied to the tampon applicator.

To achieve the desired properties of the coating composition on the tampon applicator, it has been found that the coating should be applied in a thickness of about 2 microns to about 50 microns. Preferably, the coating has a thickness of about 3 microns to about 6 microns.

EXAMPLES

The following examples or embodiments are meant to exemplify the many novel modifications that may be made to one or more inner layers of a tampon applicator in accordance with the present invention and in no way are intended to limit the invention.

In an embodiment of the present invention, a tampon applicator barrel and plunger may include the same inner layer modifications, thus resulting in uniform aesthetic and/or functional properties across the entire applicator. By way of example, and referring to FIG. 1, one or both of inner layers 28, 30 and inner layers 42, 44 may have one or more of the same optical enhancing materials, such as, but not limited to, colorants, pigments, dyes, pearlescence, or any combinations thereof. As a result, the optical enhancement would be present across the entire tampon applicator 10.

In another embodiment of the present invention, inner layers 28, 30 are modified and/or include different material than inner layers 42, 44. As a result, barrel 20 will have different aesthetic and/or functional properties than those associated with plunger 40. This is especially valuable when one might desire, for example, a low coefficient of friction on the barrel, yet enhanced grippability on the plunger. This can be easily achieved by the present invention by varying the material/modification to the inner layer(s) of barrel 20 and plunger 40.

Figure 2:
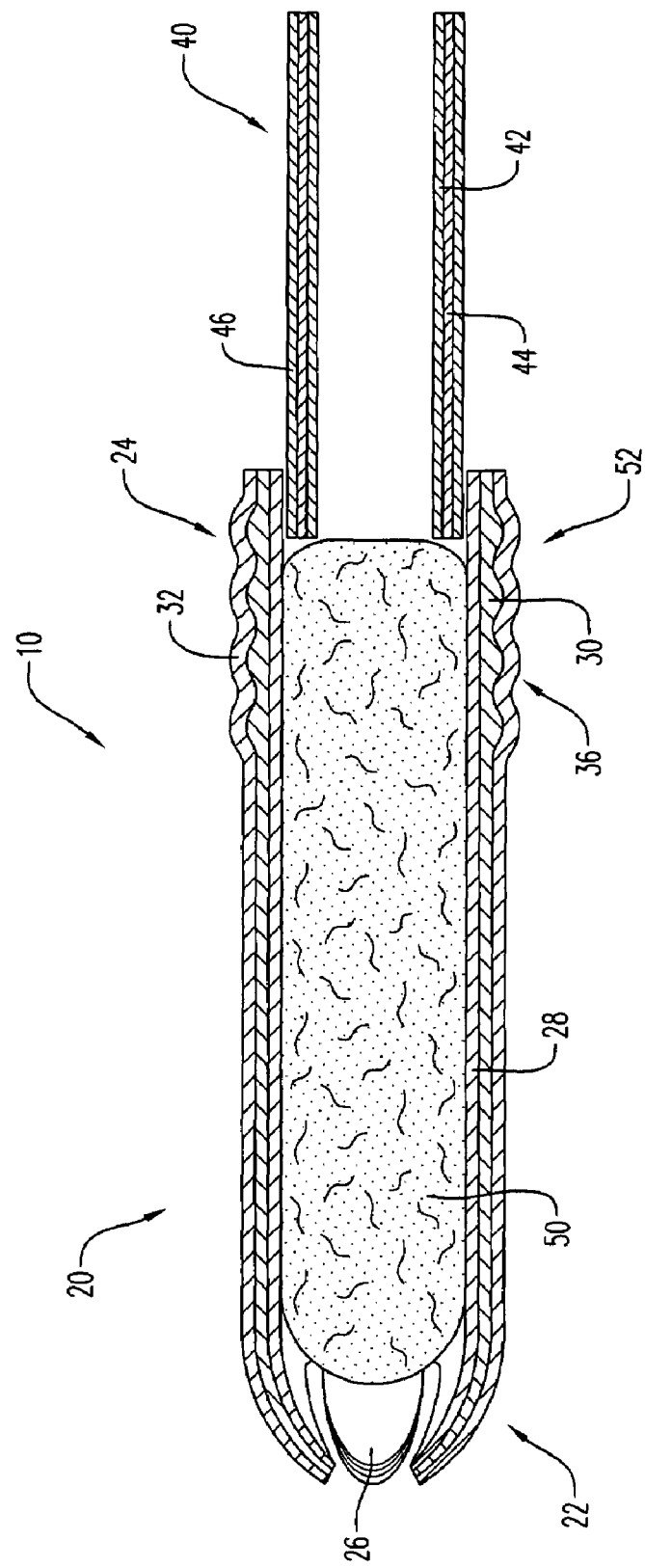
FIG. 2 is a cross-sectional view of a multiple-layer tampon applicator having an inner layer modification that forms a fingergrip according to the present invention.

In yet another embodiment according to the present invention, a fingergrip area may be formed on the withdrawal end of the tampon applicator barrel by modifying a discrete area of one or more of the inner layers that make up the barrel. Referring to FIG. 2, tampon applicator 10 has barrel 20 with withdrawal end 24. Inner layer 30 has been modified with one or more modifications according to the present invention resulting in a raised or textured surface 36 in fingergrip region 52 at withdrawal end 24.

It should be understood that the principles described above with respect to FIG. 1 and FIG. 2 may be applied to any portion or any area of the tampon applicator barrel, plunger, or both. The ability to provide such modifications during the initial formation of the tampon applicator eliminates the need for further processing to form, for example, a fingergrip. As a result, substantial time and cost efficiencies may result.

In another embodiment of the present invention, at least one inner layer of a tampon applicator is modified to be colored, which results in a colored applicator. The modification can include a colored coating material, such as pigmented wax, or may include colored paper or plastic material. The modification to the one or more inner layers may be uniform or may be done to effectuate any desired multi-colored or patterned effect on any portion of the applicator. Additionally, the applicator may include an outer layer coating or resin, wax or combination thereof, in accordance with the present invention.

In another embodiment of the present invention, at least one inner layer of a multiple-layered tampon applicator includes an embossed paper layer. Preferably, the embossments are patterned across the entire applicator and are not confined to any single area. Also, this applicator may include a coating to form the outer layer, according to the present invention.

In another embodiment of the present invention, the one or more inner layers are modified to include lubricant. The tampon applicator also includes an outer coating material, such as wax, resin or any combinations thereof. The lubricant is capable of migrating through, into, or onto the surface of the outer layer to provide lubrication to a user of the tampon applicator.

Other modifications of the present invention will be obvious to those skilled in the art in the foregoing teachings. Moreover, while the present invention has been described with reference to specific embodiments and particular details thereof, it is not intended that these details be construed as limiting the scope of the invention.

Wherefore we claim:

1. A cardboard tampon applicator comprising one or more inner layers, wherein said one or more inner layers have at least one modification that provides said tampon applicator with enhanced aesthetic and/or functional properties compared to a tampon applicator without said at least one modification, wherein said at least one modification includes one or more optical enhancing materials, wherein said one or more optical enhancing materials is a coating, wherein said coating further comprises one or more optical components selected from the group consisting of mica, TiO$_2$-coated mica, iron oxide coated mica, bismuth oxychloride, holographic material, pearlescence material, reflective material, glitter, metallic effect pigment, interference pigment, liquid crystal effect material, and any combinations thereof; and
   wherein said tampon applicator comprises a barrel having one or more inner layer coating modifications and a plunger having one or more inner layer coating modifications, and wherein said one or more barrel modifications are different than said one or more plunger modifications.

2. The tampon applicator of claim 1, wherein said tampon applicator comprises a barrel, a plunger, a fingergrip, one or more insertion petals, and any combinations thereof.

3. The tampon applicator of claim 1, wherein said coating comprises resin, wax and any combinations thereof.

4. The tampon applicator of claim 3, wherein said coating comprises resin selected from the group consisting of epoxy, acrylic, urethane, polyester, silicone, UV curable epoxy, UV curable acrylic, electron beam curable epoxy, electron beam curable acrylic, UV curable silicone, electron beam curable silicone, thermally curable silicone, modified resins such as styrenated acrylic, epoxy acrylate, polyester acrylate, polyester, vinyl ester, vinyl ether, vinyl chloride, polyvinyl alcohol, polyvinyl acetate, and any combinations thereof.

5. The tampon applicator of claim 1, wherein said one or more optical components are included in said coating in an amount about 1 weight percent (wt. %) to about 70 wt. %, based on the total weight of the coating.

6. The tampon applicator of claim 1, wherein said coating comprises one or more color components.

7. The tampon applicator of claim 6, wherein said one or more color components is selected from the group consisting of colorants, dyes, inorganic pigments, organic pigments, and any combinations thereof.

8. The tampon applicator of claim 6, wherein said one or more color components is one or more pigments selected from the group consisting of titanium dioxide, white titanium dioxide, iron oxide, red iron oxide, orange iron oxide, white zinc sulfide, aluminum powder, bronze powder, Red Lake C, phthalocyanine green, phthalocyanine blue, phthalocyanine red, diarylide yellow, quinacridone red, rhodamine red, lithol rubine red, napthol red, neozapon red, carbizole violet, carbon black, and any combinations thereof.

9. The tampon applicator of claim 6, wherein said one or more color components are present in said coating in an amount about 0.001 wt. % to about 5 wt. %, based on the total weight of said coating.

10. The tampon applicator of claim 1, wherein said coating comprises one or more optical components and one or more color components.

11. The tampon applicator of claim 1, further comprising one or more surface modification materials, wherein said one or more surface modification materials are selected from the group consisting of lubricant, surface hardness modifier, surface softness modifier, abrasive material, hydrophilic material, hydrophobic material, polyurethane, acrylic, PVC, silicone, PTFE, paraffin, phenol, fluoropolymer, polyester, epoxy, vinyl, polyamideimide, PPS, nylon, parylene, urethane, polyamide, polysulfide, Penford Gum 280 Starch, cast-coated paper, lubricious paper, sprayed paper, and any combinations of the above.

12. The tampon applicator of claim 1, further comprising an outer layer.

13. The tampon applicator of claim 12, wherein said outer layer is selected from the group consisting of coating, paper, plastic, and any combinations thereof.

14. The tampon applicator of claim 13, wherein said outer layer is a coating selected from the group consisting of resin, wax and any combinations thereof.

15. The tampon applicator of claim 14, wherein said resin is selected from the group consisting of epoxy, acrylic, urethane, polyester, silicone, UV curable epoxy, UV curable acrylic, electron beam curable epoxy, electron beam curable acrylic, UV curable silicone, electron beam curable silicone, thermally curable silicone, modified resins such as styrenated acrylic, epoxy acrylate, polyester acrylate, polyester, vinyl ester, vinyl ether, vinyl chloride, polyvinyl alcohol, polyvinyl acetate, and any combinations thereof.

16. The tampon applicator of claim 13, wherein said coating further comprises one or more optical components selected from the group consisting of mica, TiO$_2$-coated mica, iron oxide coated mica, bismuth oxychloride, holographic material, pearlescence material, reflective material, glitter, metallic effect pigment, interference pigment, liquid crystal effect material, and any combinations thereof.

17. The tampon applicator of claim 16, wherein said one or more optical components are included in said coating in an amount about 1 weight percent (wt. %) to about 70 wt. %, based on the total weight of the coating.

18. The tampon applicator of claim 13, wherein said coating comprises one or more color components.

19. The tampon applicator of claim 18, wherein said one or more color components is selected from the group consisting of colorants, dyes, inorganic pigments, organic pigments, and any combinations thereof.

20. The tampon applicator of claim 18, wherein said one or more color components is one or more pigments selected from the group consisting of titanium dioxide, white titanium dioxide, iron oxide, red iron oxide, orange iron oxide, white zinc sulfide, aluminum powder, bronze powder, Red Lake C, phthalocyanine green, phthalocyanine blue, phthalocyanine red, diarylide yellow, quinacridone red, rhodamine red, lithol rubine red, napthol red, neozapon red, carbizole violet, carbon black, and any combinations thereof.

21. The tampon applicator of claim 18, wherein said one or more color components are present in said coating in an amount about 0.001 wt. % to about 5 wt. %, based on the total weight of said coating.

22. The tampon applicator of claim 13, wherein said coating comprises one or more optical components and one or more color components.

23. The tampon applicator of claim 1, wherein said tampon applicator has a barrel and a plunger and said one or more inner layer modifications are uniformly applied to both said barrel and plunger.

24. The tampon applicator of claim 1, wherein said tampon applicator has a barrel with one or more inner layer modifications to one or more discrete areas of said barrel.

25. The tampon applicator of claim 1, wherein said tampon applicator has a plunger with one or more inner layer modifications to one or more discrete areas of said plunger.

26. A cardboard tampon applicator comprising at least one colored inner layer, wherein said at least one colored inner layer is selected from the group consisting of colored coating material, colored wax, colored resin, colored paper, colored plastic, and any combinations thereof, said inner layer having an optical enhancing material such as a coating, wherein said coating further comprises one or more optical components selected from the group consisting of mica, $TiO_2$-coated mica, iron oxide coated mica, bismuth oxychloride, holographic material, pearlescence material, reflective material, glitter, metallic effect pigment, interference pigment, liquid crystal effect material, and any combinations thereof; and wherein said tampon applicator comprises a barrel having one or more inner layer coating modifications and a plunger having one or more inner layer coating modifications, and wherein said one or more barrel modifications are different than said one or more plunger modifications.

27. The tampon applicator of claim 26, further comprising an outer layer selected from the group consisting of resin coating, wax coating, and any combination thereof.

28. A method for making a cardboard tampon applicator having one or more inner layers comprising the step of:

modifying said one or more inner layers with one or more optical enhancing materials, wherein said one or more optical enhancing material is a coating, wherein said coating further comprises one or more optical components selected from the group consisting of mica, $TiO_2$-coated mica, iron oxide coated mica, bismuth oxychloride, holographic material, pearlescence material, reflective material, glitter, metallic effect pigment, interference pigment, liquid crystal effect material, and any combinations thereof;

wherein said tampon applicator comprises a barrel having one or more inner layer coating modifications and a plunger having one or more inner layer coating modifications, and wherein said one or more barrel modifications are different than said one or more plunger modifications; and wherein said tampon applicator has enhanced aesthetic and/or functional properties compared to a tampon applicator without modifying one or more inner layers.

29. The method of claim 28, further comprising the step of applying an outer layer to said tampon applicator.

30. The method of claim 29, wherein said outer layer is selected from the group consisting of resin, wax and any combinations thereof.

* * * * *